(12) United States Patent
Juo et al.

(10) Patent No.: US 8,420,618 B2
(45) Date of Patent: Apr. 16, 2013

(54) MICRORNA-BASED METHOD FOR ANTI-COLORECTAL CANCER EFFECTS AND PROGNOSIS OF COLORECTAL CANCER

(75) Inventors: Suh-Hang Hank Juo, Kaohsiung (TW); Jaw-Yuan Wang, Kaohsiung (TW); I-Ping Yang, Kaohsiung (TW); Hsiang-Lin Tsai, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/166,234

(22) Filed: Jun. 22, 2011

(65) Prior Publication Data

US 2012/0329853 A1     Dec. 27, 2012

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search .................. None
See application file for complete search history.

(56) References Cited

PUBLICATIONS

Jianyin Long et al., Identification of MicroRNA-93 as a Novel Regulator of Vascular Endothelial Growth Factor in Hyperglycemic Conditions, The Journal of Biological Chemistry, Jul. 23, 2010, pp. 23457-23465, vol. 285, No. 30.

Aaron J. Schetter et al., MicroRNA Expression Profiles Associated with Prognosis and Therapeutic Outcome in Colon Adenocarcinoma, JAMA, Jan. 30, 2008, pp. 425-436, vol. 299, No. 4.

*Primary Examiner* — Amy Bowman
(74) *Attorney, Agent, or Firm* — WPAT, P.C.; Anthony King

(57) ABSTRACT

The present invention discloses a method of providing anti-oncogenic effects in a subject suffered from colorectal cancer. The present invention also discloses a method for screening an anti-colorectal cancer agent. The present invention further discloses a method of determining the prognosis of a subject with colorectal cancer.

4 Claims, 5 Drawing Sheets
(1 of 5 Drawing Sheet(s) Filed in Color)

(A)

(B)

(C)

(D)

US 8,420,618 B2

MICRORNA-BASED METHOD FOR ANTI-COLORECTAL CANCER EFFECTS AND PROGNOSIS OF COLORECTAL CANCER

FIELD OF THE INVENTION

The present invention relates to a method of providing anti-oncogenic effects in a subject suffered from colorectal cancer. This invention also relates to a method for screening an anti-colorectal cancer agent. This invention further relates to a method of determining the prognosis of a subject with colorectal cancer.

BACKGROUND OF THE INVENTION

A microRNA (miR) is a noncoding small RNA that contains 17-25 nucleotides. A miR can post-transcriptionally regulate the expression of several target genes through directly binding to their 3' untranslational regions (3'UTR). The annealing of the miR to the mRNA then inhibits protein translation, but sometimes facilitates cleavage of the mRNA. Through regulation of a miR's target genes, miRs have been suggested to play a role in the development of cancer carcinogenesis, progression and recurrence. Although miR attracted a great deal of attentions in the biomedicine field in the past few years, most of their functions in disease progress are yet to be confirmed.

Colorectal cancer is one of the most common cancers and has a very high recurrence and mortality rate. Effectively distinguish patients with poor prognosis will be helpful for patients follow-up and treatment. At present, there is no ideal biomarker to reliably predict the colorectal cancer recurrence.

U.S. application Ser. No. 12/398,852, hereby incorporated by reference, discloses methods and compositions for identifying a miRNA (miR) profile for a particular condition, such as colorectal cancer, and using the profile in the diagnosis and/or prognosis of a patient for a condition, such as colorectal cancer and colorectal cancer recurrence or response to therapy. The U.S. application Ser. No. 12/398,852 used the hybridization method in the microarray for large-scale screening. Nevertheless, the microarray data from the hybridization experiments is subject to false positive results. It is desirable that more reliable methods and more functional studies should be identified to validate the relation between miR and colorectal cancer recurrence.

It is always desirable to search for a better or other alternative method for anti-tumorigenesis and anti-recurrence. The present invention addresses the need by disclosing a method of anti-colorectal cancer or anti-colorectal cancer recurrence, a method for screening an anti-colorectal cancer agent and a method of determining the prognosis of a subject with colorectal cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
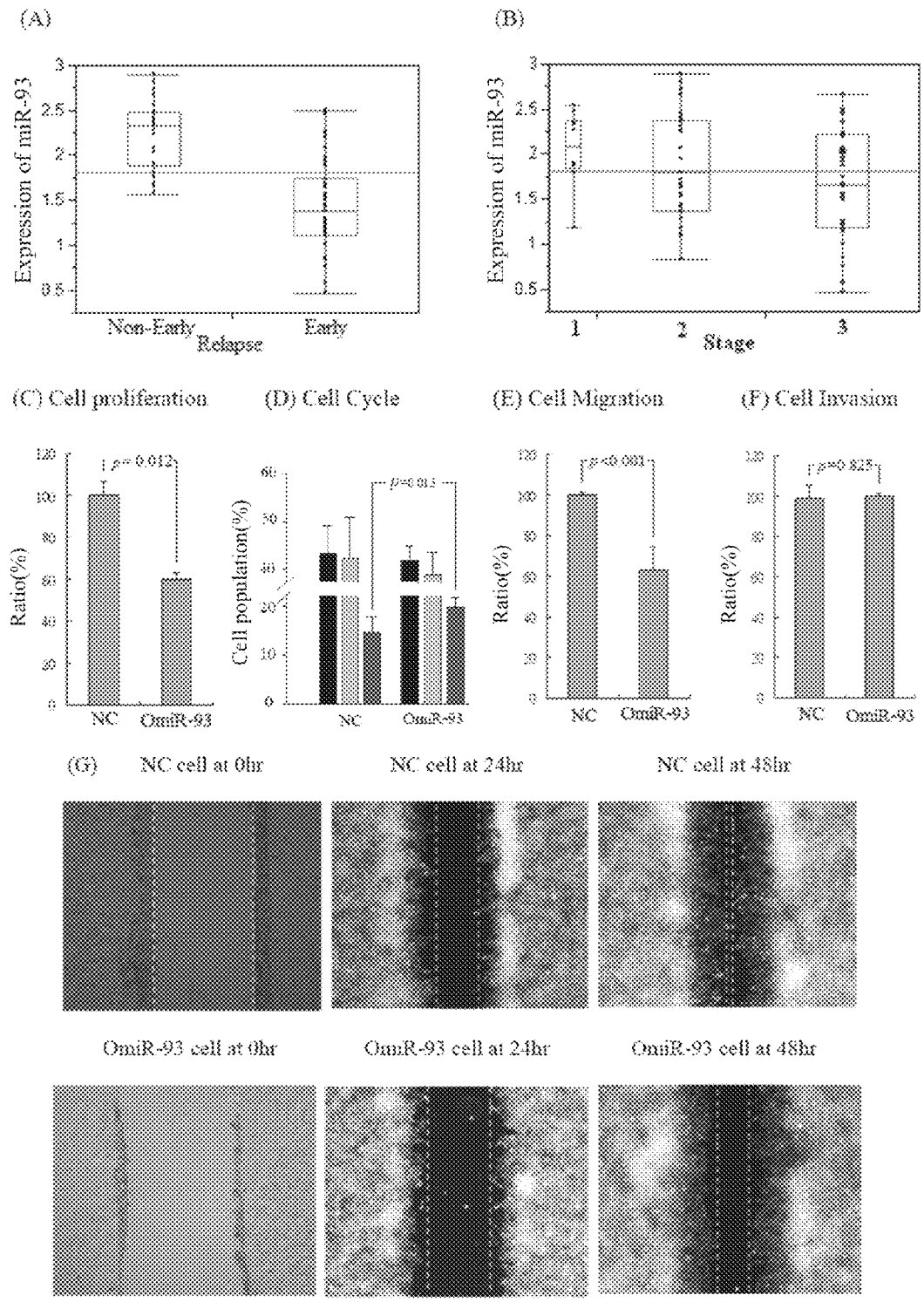
FIG. 1. (A) miR-93 expression levels in 35 non-early and 42 early relapsed CRC samples. The relative expression level of miR-93 is $\log_{10} (2^{-\Delta Ct})$. $\Delta Ct=(CT_{miR-93}-CT_{U6b})$ and U6b is as an internal control for normalization. The difference of expression level significantly decreases in the early relapsed samples (p<0.0001 with adjustment for age, sex and stage of CRC tumor). (B) The mean of miR-93 expression levels in different stages of CRC samples (stage I: n=10, stage II: n=35 and stage III: n=32). There is a monotonic decrease of expression level along with in the advance of CRC stage (p=0.0325 with adjustment for age, sex of CRC). (C) miR-93 suppresses tumor cell proliferation according to the WST-1 assay, p=0.012. OmiR-93 indicates the stable clone over-expressing miR-93 and NC indicates the negative control stable clone. (D) Over-expression of miR-93 causes significant accumulation of cells in the G2 phase, p=0.013 (black: G0 phase; light gray: S phase and dark gray: G2 phase). (E) Over-expression of miR-93 suppresses tumor cell migration according to the Transwell assay, p<0.001. (F) Over-expression of miR-93 can not affect the tumor cell invasion, p=0.825. (G) Over-expression of miR-93 cells decreases migration capability indicated by a wider gap at 24 hr and 48 hr. The photographs of tumor cell migration are from the wounding healing assay.

The present invention discloses a method of providing anti-oncogenic effects in a subject suffered from colorectal cancer in which miR-93 expression level is lower in cancer cells of case subject relative to a control subject, comprising administering to the subject an effective amount of miR-93, or miR-93 mimics.

The present invention also discloses a method for screening an anti-colorectal cancer agent, comprising providing a test agent to a cell and measuring the level of at least one miR associated with decreased expression levels in colorectal cancer cells, wherein an increase in the level of miR in the treated cell, relative to a control cell, is indicative of the test agent being an anti-colorectal cancer agent.

The present invention further discloses a method of determining the prognosis of a subject with colorectal cancer, comprising measuring the level of at least one miR in a test sample from said subject, wherein an alteration in the level of the at least one miR in the test sample, relative to the level of a corresponding miR in a control sample, is indicative of predicting recurrence of colorectal cancer.

DETAILED DESCRIPTION OF THE INVENTION

Colorectal cancer (CRC) is a significant problem in public health; there are nearly one million new cases of CRC diagnosed world-wide each year and approximately half a million deaths. For many decades, the depth of tumor invasion, regional lymph node involvement, and the presence or absence of distant metastasis have been used as major prognostic factors to predict the postoperative relapse in CRC patients by American Joint Commission on Cancer/International Union Against Cancer (AJCC/UICC) staging. Although surgical resection can be highly effective for a localized disease, 25% to 40% of patients developed recurrence after surgery, and one-third of them had local recurrence and the others developed distant metastases. The recurrence of CRC is for the most part a time-limited phenomenon, and 40-50% of recurrences become apparent within the first year after initial resection. It has been shown that time from the initial treatment to recurrence was strongly related to survival, particular within one year after surgical resection. Continuous efforts have been made to improve the method for the early detection of tumors in order to provide adequate and effective treatment to improve patient prognosis. At present, there is no ideal biomarker or indicator to differentiate early relapsed patients from non-early relapsed patients. A simple and reliable biomarker for the detection of postoperative early relapse would help physicians to undergo more aggressive treatments and also assist patients to arrange their life schedules.

The tumorigenesis of CRC involves multi-step genomic changes including activation of oncogenes and inactivation of tumor suppressor genes. Recently, emerging evidence has suggested that deregulated miRs are involved in the pathogenesis of CRC. Although several reports have demonstrated miRs in relation to the development of CRC, studies focused on the association between miRs and early relapse of CRC are sparse.

In the present invention, miR arrays were used to compare the miR profiling between the CRC tissues of early and non-early recurrence. The cutoff point to define early or non-early relapse is based on the recurrence of CRC within 12 months after radical surgery. The role of miR-93 was then validated in more tissues samples. A series of in vitro and in vivo embodiments were then conducted to validate and illustrate the role of miR-93 in regard to CRC recurrence.

MiR-93 had substantial difference of expression levels between early (recurrence within 12 months after surgery) and non-early relapse of CRC. Further embodiment including 35 early relapsed and 42 non-early relapsed CRC confirmed a high level of miR-93 in non-early relapsed samples. Cellular experiment showed that over-expression of miR-93 inhibited colon cancer cell proliferation and migration but not invasion. The cell cycle results revealed that miR-93 causes accumulation of the G2 population. However, miR-93 could not induce cell apoptosis or necrosis. Functional results showed that miR-93 could suppress CCNB1 (cyclin B1) protein expression leading to cell cycle arrest in the G2 phase. Moreover, miR-93 could repress expression of ERBB2, p21 and VEGF, all of which are involved in cell proliferation. MiR-93 also suppressed tumor growth in null mice. Taken together, the present invention demonstrated that miR-93 inhibits tumorigenesis and reduces CRC early recurrence, which may have potential clinical applications for the prediction and intervention of CRC patients.

The anti-oncogenic effects including inhibition of colon cancer cell proliferation, migration, angiogenesis and tumor growth.

The term "anti-colorectal cancer", as used herein, is intended to mean inhibitive of the growth of cancer cells and/or suppressive or oppressive of the metastasis of cancer cells or inhibitive of early recurrence which refers to any action resulting in the suppression of tumorigenesis or the prolongation of cancer remission or the reduction of recurrence through the administration of anti-colorectal cancer agent.

Therefore, the present invention provides a method of providing anti-oncogenic effects in a subject suffered from colorectal cancer in which miR-93 expression level is lower in cancer cells of case subject relative to a control subject, comprising administering to the subject an effective amount of miR-93, or miR-93 mimics. In a preferred embodiment, the case subject is early relapse and the control subject is non-early relapse. The miR-93 down-regultes CCNB1, ERBB2, P21 and VEGF genes.

As defined herein, the term "mimics" is refer to any nucleic acid that mimic endogenous mature miRNA molecules.

The present invention also provides a method for screening an anti-colorectal cancer agent, comprising providing a test agent to a cell and measuring the level of at least one miR associated with decreased expression levels in colorectal cancer cells, wherein an increase in the level of miR in the treated cell, relative to a control cell, is indicative of the test agent being an anti-colorectal cancer agent. In a preferred embodiment, the miR gene product is miR-93.

The present invention further provides a method of determining the prognosis of a subject with colorectal cancer, comprising measuring the level of at least one miR in a test sample from said subject, wherein an alteration in the level of the at least one miR in the test sample, relative to the level of a corresponding miR in a control sample, is indicative of predicting colorectal cancer early recurrence after surgery. In a preferred embodiment, the miR gene product is miR-93. In a preferred embodiment, the case subject is early relapse and the control subject is non-early relapse.

EXAMPLES

The examples below are non-limiting and are merely representative of various aspects and features of the present invention.

Patients and Tumor Samples

Two cohorts of CRC patients were recruited. The first cohort included 77 subjects with primary CRC in UICC stages I-III (35 non-early relapse and 42 early relapse after radical resection). The development of new post-operative recurrent or metastatic lesions was defined as postoperative relapse. Early relapse was defined as local recurrence (tumor growth restricted to the anastomosis or the region of the primary operation) or distant metastasis (distant metastasis or diffuse peritoneal seeding) within 1 year after radical resection. The first cohort was used to disclose miRs related to early recurrence. To test whether the candidate miRs are also differentially expressed between paired tumor and non-tumor colorectal samples of a same subject, the second cohort that comprised 45 CRC patients for this experiment were further recruited. To avoid the potential influence of neoadjuvant treatment on miR expression, patients were excluded if they had undergone neoadjuvant treatment with either chemotherapy or radiotherapy before surgery. All subjects were unrelated ethnic Chinese residing in Taiwan. Human tissues were quickly frozen in liquid nitrogen after surgical resection. All clinical samples were obtained with the informed consent from each subject, and the study protocol was approved by the local Institutional Review Board.

Statistical Analysis

A continuous variable was presented as mean±standard deviation (SD), and a dichotomous variable was presented as number and percent. The ANCOVA statistical method was performed with the JMP software (version 7.0.1, SAS Institute Inc., Cary, N.C.) to compare the mean of miR expression between subjects of early and non-early relapse with adjustment for age, sex and stage of CRC patients. A two-tailed p value less than 0.05 was considered statistically significant.

Results: Demographic Data

The characteristics of the first cohort of 77 independent CRC patients (35 non-early relapse and 42 early relapse) are summarized in Table 1. Their mean age (yr) was 66.4 with the range from 24 to 86 years old. The status regarding the early recurrence in this cohort is shown in Table 2. The second cohort that comprised 45 patients were used to compare miR-93 expression levels between paired tumor and non-tumor colorectal samples from the same individual (summarized in Table 3). The mean age (yr) of the second cohort was 65.8 with the range from 37 to 84 years old. Patients of early relapse had more advanced stages than non-early relapsed patients (p=0.003, Table 2), but their age and sex distributions were not significantly different.

TABLE 1

Clinicopathologic characteristics of 77 UICC[a] stage I-III colorectal cancer patients who were included as Cohort I of the present example

| Variables | Number (%) |
|---|---|
| Gender male/female | 42(54.5)/35(45.5) |
| Age (y/o) <65/≧65 | 28(36.4)/49(63.6) |

TABLE 1-continued

Clinicopathologic characteristics of 77 UICC[a] stage I-III colorectal cancer patients who were included as Cohort I of the present example

| Variables | Number (%) |
|---|---|
| Maximum size (cm) <5/≧5 | 43(55.8)/34(44.2) |
| Location colon/rectum | 50(64.9)/27(35.19) |
| Stage I/II/III | 10(13.0)/35(45.5)/32(41.56) |
| Depth of invasion $T_1/T_2/T_3/T_4$ | 2(2.6)/11(14.3)/60(77.9)/4(5.2) |
| Vascular invasion no/yes | 56(72.7)/21(27.3) |
| Perineural invasion no/yes | 55(71.4)/22(28.6) |
| Histology WD/MD/PD[b] | 5(6.5)/63(81.8)/9(11.7) |
| Type of tumor A/M[c] | 68(88.3)/9(11.7) |
| Early relapsed no/yes | 35(45.5)/42(54.5) |

[a]International Union Against Cancer
[b]WD: Well differentiated; MD: Moderately well differentiated; PD: Poorly differentiated
[c]A: Adenocarcinoma; M: Mucinous carcinoma
[d]Early relapse

TABLE 2

Age, sex and UICC stage between non-early relapsed and early relapsed colorectal cancer patients

|  | Non-Early | Early | P value |
|---|---|---|---|
| N | 35 | 42 |  |
| Age | 68.3 ± 12.3 | 64.8 ± 13.9 | 0.25 |
| Sex (F/M) | 17 (48.6) | 18 (42.9) | 0.61 |
| UICC[a] |  |  |  |
| Stage I | 8 (22.9%) | 2 (4.8%) |  |
| Stage II | 19 (54.3%) | 16 (38.1%) | 0.003 |
| Stage III | 8 (22.9%) | 24 (57.1%) |  |

[a]International Union Against Cancer

TABLE 3

Clinicopathologic characteristics of 45 UICC[a] stage I-III colorectal cancer patients in the second cohort II of the present example

| Variables | Number (%) |
|---|---|
| Gender male/female | 27(60.0)/18(40.0) |
| Age (y/o) <65/≧65 | 18(40.0)/27(60.0) |
| Maximum size (cm) <5/≧5 | 23(51.1)/22(48.9) |
| Location colon/rectum | 34(75.6)/11(24.4) |
| Stage I/II/III | 7(15.6)/18(40.0)/20(44.4) |
| Depth of invasion $T_1/T_2/T_3/T_4$ | 3(6.7)/5(11.1)/28(62.2)/9(20.0) |
| Vascular invasion yes/no | 15(33.3)/30(66.7) |
| Perineural invasion yes/no | 8(17.8)/37(82.2) |

TABLE 3-continued

Clinicopathologic characteristics of 45 UICC[a] stage I-III colorectal
cancer patients in the second cohort II of the present example

| Variables | Number (%) |
|---|---|
| Histology WD/MD/PD[b] | 0(0)/37(82.2)/8(17.8) |
| Type of tumor A/M[c] | 38(84.4)/7(15.6) |

[a]International Union Against Cancer
[b]WD: Well differentiated; MD: Moderately well differentiated; PD: Poorly differentiated
[c]A: Adenocarcinoma; M: Mucinous carcinoma RNA Extraction and cDNA Preparation Approximately 100 mg of each tissue was homogenized using a bench-top homogeniser (Polytron PT1600E, Kinematica AG, Lucerne, Switzerland) in 1 mL of TRIzol reagent (Invitrogen, Carlsbad, Calif., USA) according to the manufacturer's instructions. Total RNA that includes mRNA and miR was purified with Qiagen RNAeasy Columns (Qiagen, Hamburg, Germany). For miR array, cDNA synthesis of miRs was performed using Megaplex Reverse Transcription Human Pool A and Pool B (Applied Biosystems Inc.). For individual miR assay, cDNA of individual miR was synthesized from 20 ng of total RNA with unique primer (Applied Biosystems Inc.). For mRNA quantitative assay, cDNAs were synthesized from 1 μg of total RNA with random hexamers primers by Reverse Transcriptase (Applied Biosystems Inc.).

MicroRNA Array

Three patients with primary CRC (one non-early relapse and two early relapse) were screened by miR array (Applied Biosystems Inc., CA, USA) that contained 667 human miRs to identify differentially expressed miR between early and non-early relapse CRC. Each array contained a mammalian U6 (U6b, SEQ ID NO: 2) as an internal control. RT-qPCR was performed using the Applied Biosystems 7900HT Real-Time PCR System, and default thermal-cycling conditions by ABI 7900 Sequence detection System version 2.4.

Assay for Individual miR

For each candidate miR, TaqMan miR RT-qPCR (Applied Biosystems Inc.) assays was used to quantify the miR level. The relative expression level of miR was normalized to that of an internal control U6b (SEQ ID NO: 2) by using the equation of $\log_{10}(2^{-\Delta Ct})$, where $\Delta Ct = (CT_{miR-93} - CT_{U6b})$. The median and mean of $\log_{10}(2^{-\Delta Ct})$ and its standard deviation (SD) was calculated.

Results from microRNA Array and Follow-Up Validation

Using miR arrays, several differentially expressed miRs between the CRC tumors of early and non-early recurrent patients were identified. Among the candidate miRs, miR-93 had a decrease of expression level by 3.5-fold in early relapsed samples compared to non-early relapsed samples.

To further confirm that miR-93 expression levels were different between early and non-early relapsed patients, additional 77 human CRC tumor samples were examined. The result showed that the expression level of miR-93 was decreased by 6.1-fold in the early recurrent samples in non-early relapsed group, and the median of $\log_{10}(2^{-\Delta Ct})$ was 2.323 in the non-early relapsed group and 1.483 in the early relapsed group (adjusted p<0.0001, FIG. 1A). The miR-93 expression in different stages of CRC tumor samples were analyzed, and an association between miR-93 expression with CRC stage was found (adjusted p=0.0325, FIG. 1B). A higher expression of miR-93 associated with early UICC stage of CRC (the median of $\log_{10}(2^{-\Delta Ct})$ was 2.077, 1.788, 1.6649 for stage I, II, III, respectively). These independent samples justified the usefulness of miR-93 in predicting the recurrence of CRC after surgery, and also warranted further functional experiments.

Results: miR-93 in the Paired Samples

Figure 4:
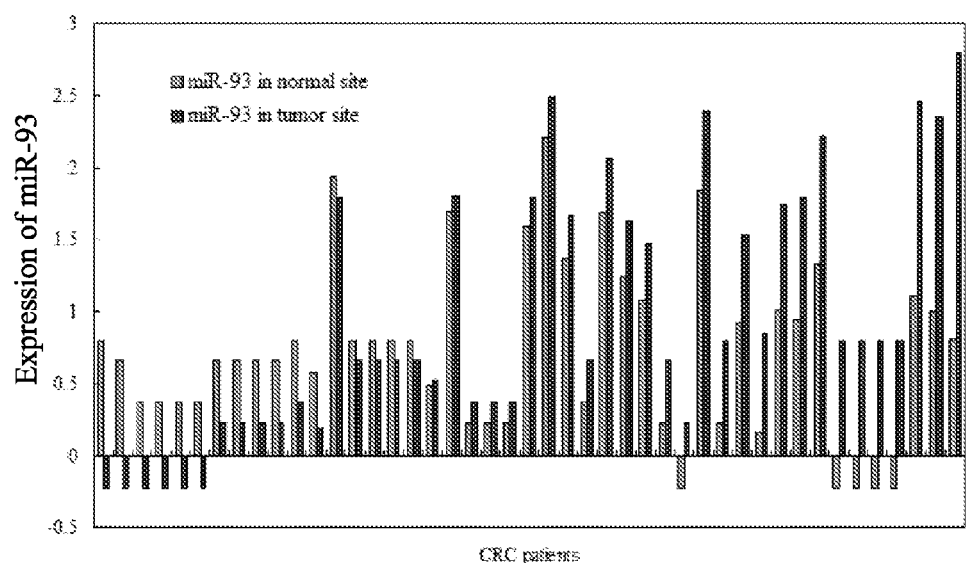
FIG. 4. miR-93 is deregulated in human colorectal cancer tumors and over-expression of miR-93 effects CCNB1 protein expression but not induces cell apoptosis. (A) The relative expression level of miR-93 detected by qPCR in the 45 paired human subjects with CRC. The relative expression level of miR-93 is $\log_{10} (2^{-\Delta Ct})$. Light gray: mir-93 expression in normal tissue. Dark gray: miR-93 expression in tumor tissue. (B) Apoptosis of Caco2 with transient transfection of scrambled miR (left) and miR-93 mimic (right) was assessed using annexin V-FITC/PI staining and flow cytometry. The x-axis (FL1 in the log scale) reflects annexin V-FITC fluorescence; the y-axis (FL3 in the log scale) reflects PI fluorescence. Early apoptotic (annexin V-FITC-positive/PI-negative) cells appear in the lower right quadrant of the dot plot (A4). Late apoptotic (annexin V-FITC-positive/PI-positive) cells appear in the upper right quadrant of the dot plot (A2). A typical result from 3 independent experiments is shown. The results show that over-expression of miR-93 does not induce cell apoptosis based on no increase of the total population that appears in the right quadrant of the dot plot (A2/A4).
Figure 4:
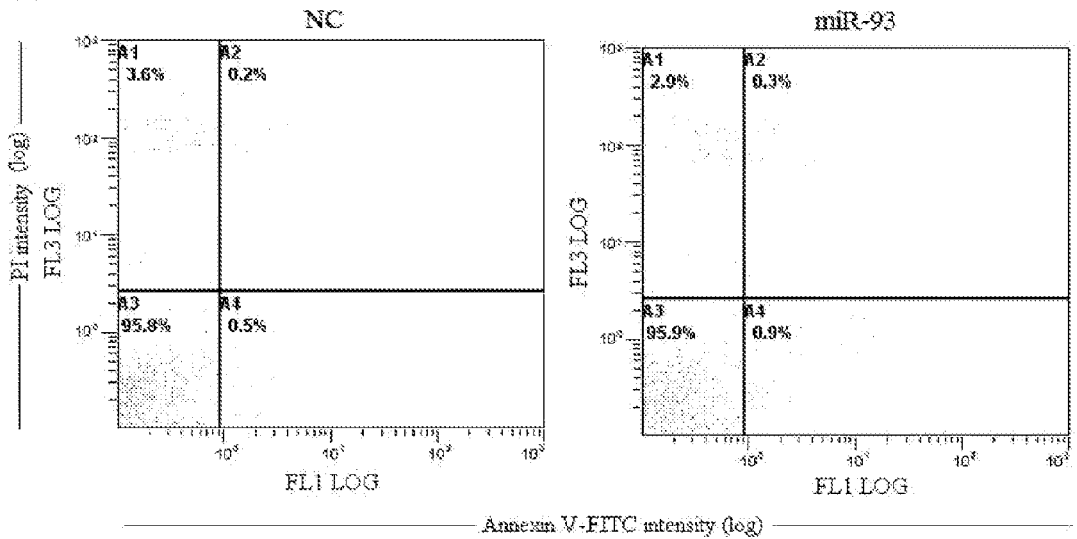

The miR-93 expression level was higher by 1.66-fold (paired t-test p=0.03) in 45 tumor tissues compared to the paired normal counterparts colorectal tissues. Among these paired samples, 62.22% (28/45) of CRC had higher miR-93 levels compared to the adjacent normal tissue (FIG. 4A).

Target Prediction

To investigate the biological functions of the miR-93, the target genes were searched using miR target prediction programs, miRDB, miRanda, miRWalk and TargetScanS. The KEGG pathway program was used to predict the pathways of the target genes.

Construction of miR-93 Over-Expressing Plasmids

The pCDH vector (System Biosciences, Mountain View, Calif., USA) was used as a miR-93 (SEQ ID NO: 1) overexpression system to assess the functional consequences of over-expressed miR-93. The pCDH-miR-93 plasmid was constructed by inserting the miR-93 PCR product (include 100 bp native flank sequence to both upstream and downstream of the microRNA stem-loop) in the 5'-to-3' orientation into the multiple cloning sites (MCS) of pCDH vector. The forward primer of miR-93 is TCCTGAATTCAACCT-TCACTGAGAGGGTGGTTG and the reverse primer is CTAGGCGGCCGCGGGAGACCAGACCCTTTTGAAC. Forward primers were elongated at the 5' ends to include the GAATTC sequence and reverse primers were elongated at 5' ends to include the GCGGCCGC sequence to create EcoR1 and Not1 restriction sites, respectively. The constructs were confirmed by direct DNA sequencing.

Cell Culture

The human colonic carcinoma cell line Caco2 (ATCC, Manassas, Va., USA) was cultured in the DMEM (Gibco-BRL, Gaithersburg, Md., USA) supplemented with 10% fetal calf serum (FCS, Gibco-BRL), 100 U/ml penicillin. The cells were maintained at 37° C. in an atmosphere of 5% $CO_2$.

Establishment of Stable Clone

The Caco2 cells ($5 \times 10^5$) were seeded to each well of a 6-well plate and incubated overnight, then transfected with 400 ng of the constructs (either negative scrambled pCDH vector (SEQ ID NO: 5) or pCDH-miR-93 plasmid) using Lipofectamine 2000 (Invitrogen Inc., Carlsbad, Calif., U.S.). The stable transfected Caco2 cells containing the pCDH-NC (negative control) or pCDH-miR-93 plasmid were selected in the standard culture media with additional 12 μg/mL puromycine (Sigma-Aldrich Co, St. Louis, USA) for four weeks and then proved by miR qRT-PCR assay.

Analysis of Cell Proliferation

Cell proliferation was determined by using the WST-1 method (Roche Diagnostics, Corp., Indianapolis, Ind., USA). Cells were seeded in a 96-well plate and incubated for 22 hr. The cells were further incubated with 1/10 volume of WST-1 reagent and incubated for another 2 hr at 37° C. before the absorbance at 450 nm was quantified in a spectrophotometer.

Analysis of Cell Cycle

Cell cycle was quantified by propidium iodide (PI, Sigma-Aldrich Co.) staining and subsequent flow-cytometric analysis. After 36-hr incubation, the cells were harvested, washed in PBS and resuspended at $10^5$/ml in PBS supplemented with 0.1% triton X-100, 0.02 mg/ml RNase and 0.05 mg/ml PI. Samples were washed with PBS to remove extract PI stain and resuspended in PBS directly analyzed on a FACScan cytofluorimeter (Becton Dickinson, Franklin Lakes, N.J., USA) using the CellQuest software (BD biosciences).

Analysis of Cell Apoptosis

For apoptosis analysis, cells were fixed in cold methanol, washed in cold PBS, and incubated with Annexin V-FITC (BD Biopharmingen) and PI (Sigma) following the manufacturer's instructions. The stained cells were subsequently analyzed by flow-cytometric analysis within 1 hr on a FACScan cytofluorometer (Becton Dickinson, Franklin Lakes, N.J., USA).

Results: Over-Expression of miR-93 Influences Cell Proliferation and Cell Cycle

To examine the potential role of miR-93 in tumorigenesis, the effect of miR-93 on the growth of Caco2 cells were evaluated first. As shown in FIG. 1C, the proliferation rate for the over-expressing miR-93 stable clone (OmiR-93) was only 60% of the rate for the negative control clone (NC) at 24 hr (p=0.012). Since the predicted target genes of miR-93 are related to the cell cycle and cell growth, miR-93 influence on the cell cycle were assessed by the flow-cytometric analysis. The results showed a significantly increased accumulation of a G2 population in the miR-93 over-expression clone (19.8% in the miR-93 over-expression clone vs. 14.7% in the negative control clone; FIG. 1D, p=0.013). Based on the results from Annexin V-FITC/PI analysis, over-expression of miR-93 did not induce cell apoptosis or necrosis (FIG. 4B). These findings suggest that over-expression of miR-93 can inhibit the growth of colon cancer cells by arresting cells in the G2 phase but cannot cause miR-93 mediated cell apoptosis.

Analysis of Cell Migration

The cell migration experiment was performed using Transwell polycarbonate membrane inserts (Millipore, GmbH, Schwalbach, Germany) in 24-well following the manufacturer's instructions. The cells were plated onto 24-well millicell at a density of $2 \times 10^4$ cells/well, and allowed to migrate for 24 hr at 37° C. The inserts were then rinsed in 1X PBS, removed the cell from the membrane with 1% Trypsin and lyses the cell with cell culture lysis reagent (Promega, Corp., Madison, Wis., USA) and the green fluorescence of the stable clone was quantified in a spectrophotometer.

Wound Healing Assay

Cells were plated onto a 6-well plate at a density of $3 \times 10^5$ cells. After cells forms a monolayer, wounded were made by manual scraping with a 200 μl micropipette tip. The culture medium was then replaced and cells were incubated at 37° C. Wound closure was monitored at various time points (0 hr, 24 hr and 48 hr) by observation under a microscope and was photographed.

Results: Effects of Over-Expression of miR-93 on Cell Migration

The transwell assay (FIG. 1E) indicated that the clone over-expressing miR-93 displayed slower migration by 63.3% when compared with the control clone (p<0.001). The inhibition of migration could also be demonstrated by the wounding healing analysis. The gap distance of control clone and the clone over-expressing miR-93 was 0.43 mm and 0.64 mm, respectively, at 24 hr; was 0.08 mm and 0.34 mm, at 48 hr. These findings suggest that the migration ability in the stable clone over-expressing miR-93 was suppressed to 65% compared with the negative control stable clone. The above results consistently exhibited the dramatically decreased migration ability after over-expression of miR-93 (FIG. 1G).

Matrigel Invasion Assay

The cell invasion ability was assayed using the 24-well Transwell permeable supports (BD biosciences, San Jose, Calif., USA) with 8-μm pore polycarbonate membrane inserts. The cells were plated on the upper chamber at a density of $1 \times 10^4$ cells following the manufacturer's instructions. After incubating at 37° C. for 24 hr, non-migrating cells were removed and migrating cells on the lower surface of the membrane were fixed and stained with crystal violet. The number of migrating cells was counted and photographed under the microscope. Three photographs from each of triplicate membranes were used for each experimental group and migrating cells were counted.

Results: Effects of Over-Expression of miR-93 on Tumor Cell Invasion

The matrigel invasion assay showed no significant difference of invasion ability between the stable clone over-expressing miR-93 (Omir-93) and control clone (NC). As shown in FIG. 1F, the finding suggests that over-expression of miR-93 dose not effect the cell invasion ability (p=0.825).

In Vivo Animal Embodiments

Four-week-old Balb/c nude mice (with body weight of 12.6 to 15.6 g) were purchased from BioLasco Taiwan Co., Ltd (Taipei, TW, R.O.C.) center and maintained in a specific pathogen free (SPF) environment (Certificate No.: 26-99S029). Each nude mouse, 6 weeks old, was injected subcutaneously with $1 \times 10^7$ Caco2 cells either NC or OmiR-93. Each group had four mice. The tumor diameter was measured daily and the tumor volume ($cm^3$) was calculated by the formula: volume=width×length×high/2 Animals were sacrificed 3 weeks after seeding tumor cells, and tumors were observed and counted immediately without prior fixation.

Results: Effect of Over-Expression of miR-93 in Nude Mice

Figure 2:
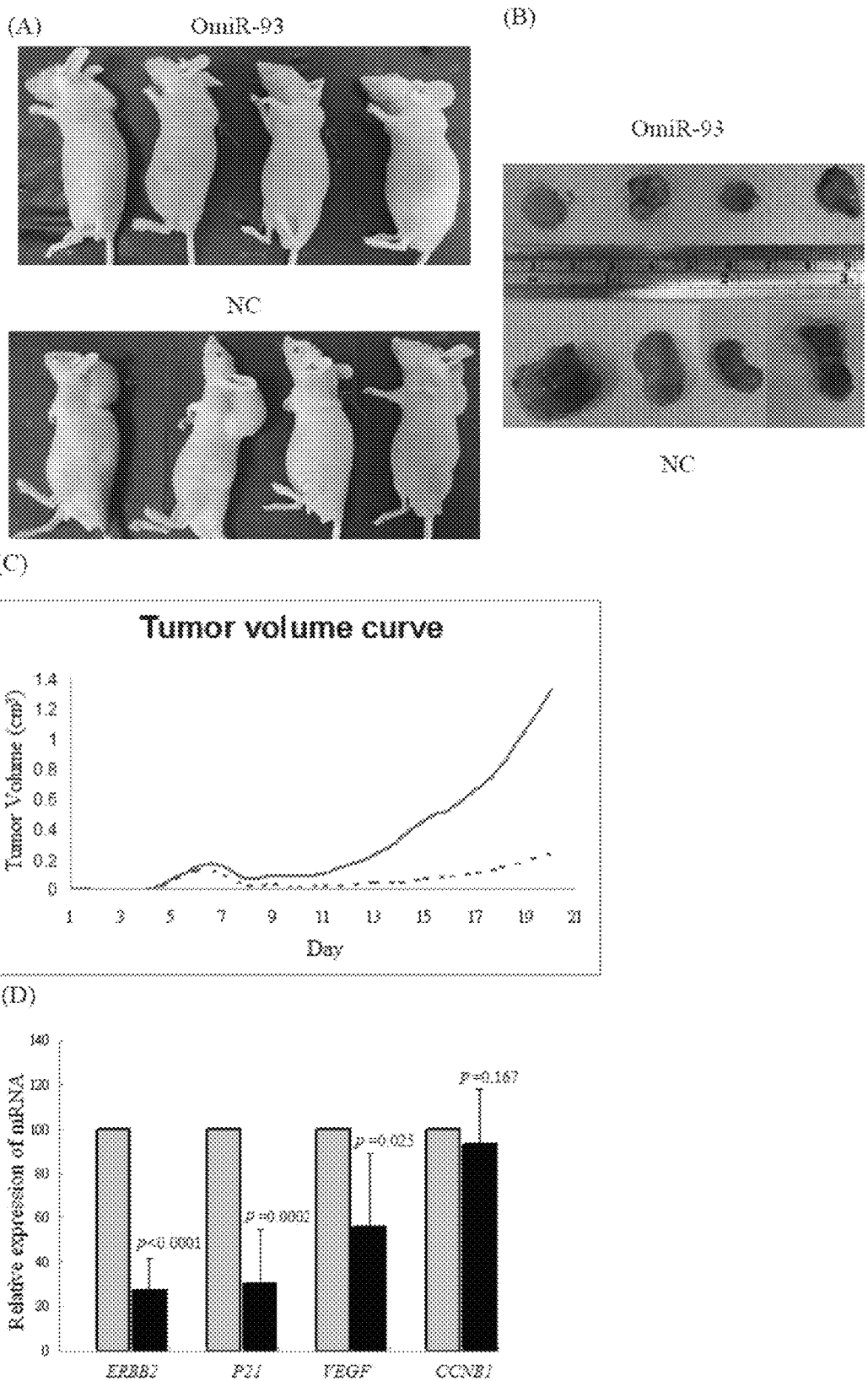
FIG. 2. Effects of miR-93 on tumor growth in an animal model and mRNA expression levels of miR-93 target genes. OmiR-93 indicates the stable clone over-expressing miR-93 and NC indicates the control stable clone. (A) At the $21^{st}$ day, null mice subcutaneously injected with OmiR-93 cells (n=4, upper) and with NC cells (n=4, below) were taken photographs. (B) Tumor lumps are drastically smaller in the OmiR-93 group (upper) than NC group (below) at the $21^{st}$ day. (C) The growth curve for tumor ($cm^3$) of OmiR-93 ( - - - ) and NC cells (—) over 21 days (p=0.005). (D) The mRNA expression level of ERBB2, p21, CCNB1 and VEGF by the qPCR. Comparing with NC (in gray), OmiR-93 (in black) expresses significantly less mRNA of ERBB2 (to 27.9%), P21 (to 26.8%) and VEGF (to 55.5%) but not CCNB1 (93.39%).

To further validate the role of miR-93 in tumorigenesis, the effect of over-expression of miR-93 on the tumor growth in vivo was evaluated. Caco2 cells stably over-expressing miR-93 (OmiR-93) and the Caco2 cells of the control clone with scrambled pCDH-NC(NC) were injected subcutaneously to allow tumor growth in nude mice. The tumors became palpable 7 days after inoculation and were allowed to grow to the end of third week (FIGS. 2A and 2C). Mice receiving OmiR-93 cells had significantly smaller (p=0.005) cancer lumps than the mice receiving NC cells. (Table 4; FIGS. 2B and 2C). This in vivo result further augmented that over-expression of miR-93 in the cancer cells resulted in a reduction of cell proliferation of the tumor lump in experimental animals.

TABLE 4

Over-expression of miR-93 in colon cancer Caco2 cell line reduces the tumorigensis ability in Balb/c nude mice

| | Tumor cells | | |
|---|---|---|---|
| | OmiR-93 | NC | P value |
| N | 4 | 4 | |
| Weight of mice, gm (day = 21) | 21.62 ± 0.79 | 22.24 ± 1.84 | 0.254 |
| Tumor size* (day = 21), $cm^3$ | 0.23 ± 0.14 | 1.33 ± 0.72 | 0.0053 |

Tumor size = (height × width × length)/2 mRNA Quantitative Assay

Reverse-transcriptase polymerase chain reaction (PCR) and then real-time PCR with SYBR Green (Applied Biosystems Inc.) were performed to quantify mRNA transcripts. cDNAs were synthesized from 1 μg of total RNA with random hexamers primers by Reverse Transcriptase (Applied Biosystems Inc.). The primers of the PCR reaction were listed in Table 5.

TABLE 5

The sequences of primers

For mRNA quantitative assay

| Gene Name | Forward primer | Reverse primer |
| --- | --- | --- |
| p21 | TTAGCAGCGGAACAAGGAGT | AGCCGAGAGAAAACAGTCCA |
| CCNB1 | GCCTCTCCAAGCCCAATGGAAAC | ACATCAGAGAAAGCCTGACACAGG |
| ERBB2 | CTACGGCAGAGAACCCAGAG | TTGATGCCAGCAGAAGTCAG |
| GAPDH | AAGGTGAAGGTCGGAGTCAA | GATCTCGCTCCTGGAAGATG |
| VEGF | AGGAGGAGGGCAGAATCATCA | CTCGATTGGATGGCAGTAGCT |

For synthesizing the full length double-stranded oligonucleotides of 3'UTR.

| Gene Name | Forward primer | Reverse primer |
| --- | --- | --- |
| CCNB1 | AAAGACTAGTCTTGTAAACTTGAGTTGGAGTAC | AAAAGAGCTCTTTTGTATTTGAGTATTGTTTTATTAAC |
| ERBB2 | GCCAACTAGTACCAGAAGGCCAAGTCCG | GGCCGAGCTCTAGCTGTTTTCCAAAATATATTTG |

Construction of Reporter Plasmids

Figure 3:
FIG. 3. miR-93 binds 3'-UTR of CCNB1 and ERBB2 and affects their protein synthesis. (A) Schematic diagram of 3'-UTR reporter construct. The 3'UTR of the target genes is inserted to the 3' end the Luc gene in the pMIR plasmid for the luciferase activity analysis. (B) The putative miR-93 binding sequence between miR-93 and 3'UTR of CCNB1 and ERBB2 was aligned. (C) OmiR-93 indicates the stable clone over-expressing miR-93 and NC indicates the control stable clone. pLuc-UTR (400 ng) transfected to OmiR-93 or NC. The luciferase activity in the OmiR-93 with the pLuc-CCNB1 plasmid is significantly lower (66.9%) compared to NC with the pLuc-CCNB1 plasmid, p=0.005. Similarly, the luciferase activity in the OmiR-93 with the pLuc-ERBB2 plasmid is significantly lower (48.43%) compared to NC with the pLuc-ERBB2 plasmid, p=0.003. (D) Western blot analysis of protein expression. OmiR-93 has lower levels of protein of miR-93 target genes than NC.
Figure 3:
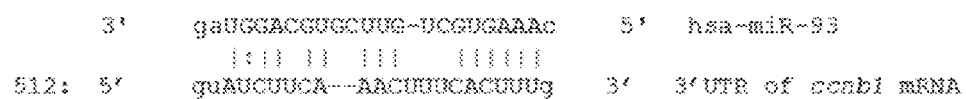
Figure 3:
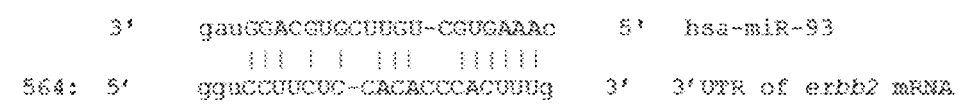
Figure 3:
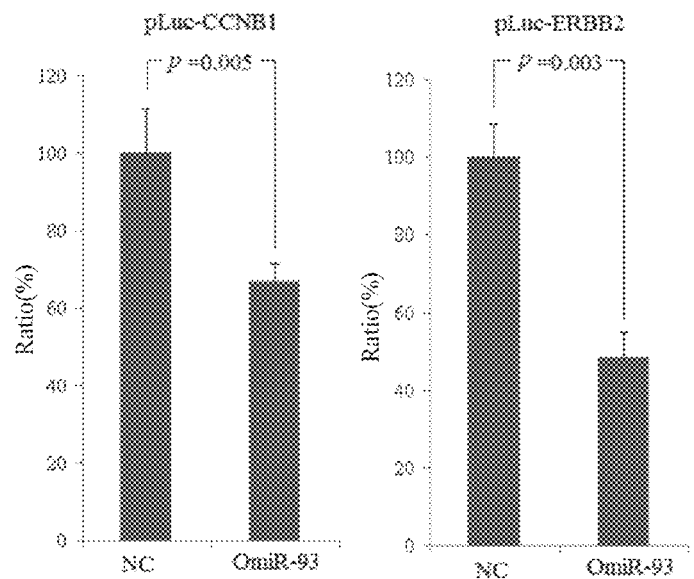
Figure 3:
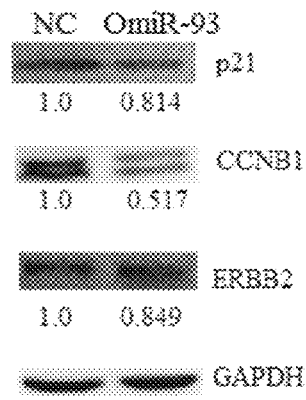

The pMIR-REPORT™ miRNA Expression Reporter Vector System (pMIR, Applied Biosystems Inc.) was used as a reporter system to assess the effect of miR-93 on protein expressions. The full length double-stranded oligonucleotides of each gene 3'UTR was synthesized by the primer pairs listed in Table 5. The reporter plasmids were constructed by inserting the PCR product of 3'UTR into the multiple cloning sites (MCS) of pMIR vector (FIG. 3A).

Transient Transfection and Luciferase Assay

The pMIR constructs (200 ng) were transfected into the cells using Lipofectamine 2000 (Invitrogen). The cells were lysed at 24 hr after transfection and the luciferase activities were measured according to the manufacturer's protocol of Luciferase Assay System (Promega). Each experiment was independently repeated three times and each sample was conducted in duplicates.

Protein Isolation and Western Blotting

Whole proteins were prepared from cell lysate with lysis buffer (Cell Signaling, Boston, Mass., USA). Protein lysates were quantified using Bio-Rad protein assay, resolved in 10% SDS-PAGE gels, and transferred to PVDF membranes and blocked in 0.1% Tween 20, 5% skim milk protein in Tris Buffer Saline. Proteins were probed with primary antibodies overnight at 4° C. The membrane was washed and visualized with horseradish peroxidase-conjugated secondary antibodies and Western Blotting Substrate (HRP) (Millipore, Billerica, Mass., USA) and exposed to ECL X-ray medical film (Konica Minolta, Mississauga, ON, Canada) to visualize bands; intensity of GAPDH bands were used to determine equal protein loading.

Antibodies

Anti-GAPDH was from Sigma-Aldrich Co; anti-cyclin B1, anti-p21, anti-ERBB2 and Alexa Fluor 594 conjugated donkey anti-rabbit IgG were from Cell Signaling Technology; and horseradish peroxidase (HRP)-conjugated goat secondary antibody was from Promega.

Immunofluorescence Staining

Immunostaining was performed following the manufacturer's instructions described (Cell Signaling). Cells were fixed for 20 minutes with cold methanol solution, washed in cold PBS, and saturated in blocking solution (3% BSA in TBS) for 1 hour. Once permeabilized with 0.3% Triton X-100 for 5 minutes, cells were incubated with primary antibody for 1 hour. After washing, sections were incubated with Alexa Fluor 594 conjugated donkey anti-rabbit IgG and nuclei were stain with DAPI (Cell Signaling). For immunostaining in the Caco2, sections were imaged on a FluoView FV1000 confocal microscope (Olympus, Hamburg, Germany).

Results: Effect of miR-93 was Mediated by CCNB1, ERBB2, P21, and VEGF

The above examples showed that miR-93 suppresses cell proliferation and migration in Caco2 cells, and arrests cancer cells in the G2 phase. Then the miR-93 target genes might be identified to elucidate the anti-oncogenic effects of miR-93. Several miR-93 target genes were predicted by bioinformatic analysis, among which CCNB1 and p21 were related to the cell cycle, and ERBB2 and VEGF were relevant to cell migration and proliferation as well as angiogenesis. The mRNA expressions of ERBB2 ($p<0.0001$), p21 ($p=0.0002$) and VEGF ($p=0.025$) were been significantly reduced in the OmiR-93 cells compared with the NC clone (FIG. 2D). Although CCNB1 mRNA expression levels were not different between two types of Caco2 clones (FIG. 2D, $p=0.167$), CCNB1 protein levels was prominently reduced by miR-93 (FIG. 3D). These results suggested that miR-93 might post-transcriptionally inhibit CCNB1 mRNA but not degrade CCNB1 mRNA.

Figure 5:
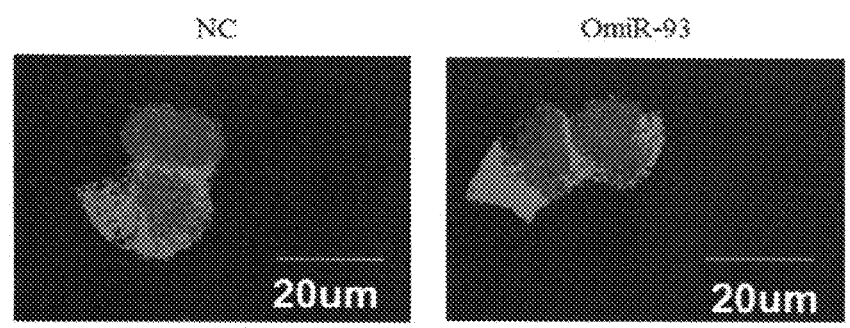
FIG. 5. Using immunofluorescence staining with CCNB1 antibody, OmiR-93 has a lower CCNB1 protein expression level (red-fluorescence) taken by the confocal microscope than NC. The blue color indicates the nuclei stained by DAPI. OmiR-93 indicates the stable clone over-expressing miR-93 and NC indicates the control stable clone. The decreased CCNB1 protein mainly located in the nucleus of OmiR-93, and cells will arrest in the G2 phase.

Since p21 and VEGF had been experimentally shown to be miR-93 target genes, only the luciferase reporter assay were conducted to confirm CCNB1 and ERBB2 as miR-93 direct target genes. The pLuc-CCNB1 and pLuc-ERBB2 plasmid constructs were generated, both of which contain the same putative miR-93 binding sequence (CACUUU) (FIGS. 3A and 3B). Based on the luciferase activity, miR-93 directly targeted the CCNB1 and ERBB2 3'UTR and down-regulated their expression levels (FIG. 3C). Western blotting also showed decreased protein levels of CCNB1, ERBB2, and p21 (FIG. 3D). Using the immunofluorescence stain with anti-CCNB1 antibody on the Caco2, the results showed that miR-93 down-regulated the intracellular CCNB1 in the Caco2 cells (FIG. 5) especially in the nucleus.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and methods are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of providing anti-oncogenic effect in a subject suffered from colorectal cancer in which miR-93 expression level is lower in cancer cells of case subject relative to a control subject, comprising administering to the subject an effective amount of miR-93, or miR-93 mimics.

2. The method of claim 1, wherein the case subject is early relapse and the control subject is non-early relapse.

3. The method of claim 1, wherein the miR-93 down-regulates CCNB1, ERBB2, P21 and VEGF genes.

4. The method of claim 1, wherein the subject is a human.

* * * * *

```
                           SEQUENCE LISTING

<160> NUMBER OF SEQ ID NOS: 19

<210> SEQ ID NO 1
<211> LENGTH: 23
<212> TYPE: RNA
<213> ORGANISM: Homo sapiens
<220> FEATURE:
<221> NAME/KEY: misc_RNA
<222> LOCATION: (1)..(23)

<400> SEQUENCE: 1
caaagugcug uucgugcagg uag                                               23

<210> SEQ ID NO 2
<211> LENGTH: 42
<212> TYPE: RNA
<213> ORGANISM: Homo sapiens
<220> FEATURE:
<221> NAME/KEY: snRNA
<222> LOCATION: (1)..(42)

<400> SEQUENCE: 2
cgcaaggaug acacgcaaau ucgugaagcg uuccauauuu uu                          42

<210> SEQ ID NO 3
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(33)
<220> FEATURE:
<221> NAME/KEY: mRNA
<222> LOCATION: (1)..(33)

<400> SEQUENCE: 3
tcctgaattc aaccttcact gagagggtgg ttg                                    33

<210> SEQ ID NO 4
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(34)

<400> SEQUENCE: 4
ctaggcggcc gcgggagacc agacccttt gaac                                    34

<210> SEQ ID NO 5
<211> LENGTH: 8189
<212> TYPE: DNA
<213> ORGANISM: Artificial Sequence
<220> FEATURE:
<223> OTHER INFORMATION: vector
```

```
<220> FEATURE:
<221> NAME/KEY: misc_feature
<222> LOCATION: (1)..(8189)

<400> SEQUENCE: 5
```

| | | | | | |
|---|---|---|---|---|---|
| acgcgtgtag | tcttatgcaa | tactcttgta | gtcttgcaac | atggtaacga | tgagttagca | 60 |
| acatgcctta | caaggagaga | aaaagcaccg | tgcatgccga | ttggtggaag | taaggtggta | 120 |
| cgatcgtgcc | ttattaggaa | ggcaacagac | gggtctgaca | tggattggac | gaaccactga | 180 |
| attgccgcat | tgcagagata | ttgtatttaa | gtgcctagct | cgatacaata | aacgggtctc | 240 |
| tctggttaga | ccagatctga | gcctgggagc | tctctggcta | actagggaac | ccactgctta | 300 |
| agcctcaata | aagcttgcct | tgagtgcttc | aagtagtgtg | tgcccgtctg | ttgtgtgact | 360 |
| ctggtaacta | gagatccctc | agacccttt | agtcagtgtg | gaaaatctct | agcagtggcg | 420 |
| cccgaacagg | gacctgaaag | cgaaagggaa | accagagctc | tctcgacgca | ggactcggct | 480 |
| tgctgaagcg | cgcacggcaa | gaggcgaggg | gcggcgactg | gtgagtacgc | caaaaatttt | 540 |
| gactagcgga | ggctagaagg | agagagatgg | gtgcgagagc | gtcagtatta | agcggggag | 600 |
| aattagatcg | cgatgggaaa | aaattcggtt | aaggccaggg | ggaaagaaaa | aatataaatt | 660 |
| aaaacatata | gtatgggcaa | gcaggagct | agaacgattc | gcagttaatc | ctggcctgtt | 720 |
| agaaacatca | gaaggctgta | gacaaatact | gggacagcta | caaccatccc | ttcagacagg | 780 |
| atcagaagaa | cttagatcat | tatataatac | agtagcaacc | ctctattgtg | tgcatcaaag | 840 |
| gatagagata | aaagacacca | aggaagcttt | agacaagata | gaggaagagc | aaaacaaaag | 900 |
| taagaccacc | gcacagcaag | cggccactga | tcttcagacc | tggaggagga | gatatgaggg | 960 |
| acaattggag | aagtgaatta | tataaatata | aagtagtaaa | aattgaacca | ttaggagtag | 1020 |
| cacccaccaa | ggcaaagaga | agagtggtgc | agagagaaaa | aagagcagtg | ggaataggag | 1080 |
| ctttgttcct | tgggttcttg | ggagcagcag | gaagcactat | gggcgcagcc | tcaatgacgc | 1140 |
| tgacggtaca | ggccagacaa | ttattgtctg | gtatagtgca | gcagcagaac | aatttgctga | 1200 |
| gggctattga | ggcgcaacag | catctgttgc | aactcacagt | ctggggcatc | aagcagctcc | 1260 |
| aggcaagaat | cctggctgtg | gaaagatacc | taaaggatca | acagctcctg | gggatttggg | 1320 |
| gttgctctgg | aaaactcatt | tgcaccactg | ctgtgccttg | gaatgctagt | tggagtaata | 1380 |
| aatctctgga | acagattgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggttaacttt | 1800 |
| taaagaaaa | gggggattg | ggggtacag | tgcagggaa | agaatagtag | acataatagc | 1860 |
| aacagacata | caaactaaag | aattacaaaa | acaaattaca | aaaattcaaa | attttatcga | 1920 |
| tactagtatt | atgcccagta | catgacctta | tgggactttc | ctacttggca | gtacatctac | 1980 |
| gtattagtca | tcgctattac | catggtgatg | cggttttggc | agtacatcaa | tgggcgtgga | 2040 |
| tagcggttg | actcacgggg | atttccaagt | ctccacccca | ttgacgtcaa | tgggagtttg | 2100 |
| ttttggcacc | aaaatcaacg | ggactttcca | aaatgtcgta | acaactccgc | cccattgacg | 2160 |
| caaatgggcg | gtaggcgtgt | acggtgggag | gtctatataa | gcagagctcg | tttagtgaac | 2220 |

```
cgtcagatcg cctggagacg ccatccacgc tgttttgacc tccatagaag attctagagc    2280
tagcgaattc gaatttaaat cggatccgcg gccgcaagga tctgcgatcg ctccggtgcc    2340
cgtcagtggg cagagcgcac atcgcccaca gtccccgaga agttgggggg aggggtcggc    2400
aattgaacgg gtgcctagag aaggtggcgc ggggtaaact gggaaagtga tgtcgtgtac    2460
tggctccgcc ttttttcccga gggtggggga gaaccgtata taagtgcagt agtcgccgtg    2520
aacgttcttt ttcgcaacgg gtttgccgcc agaacacagc tgaagcttcg aggggctcgc    2580
atctctcctt cacgcgcccg ccgccctacc tgaggccgcc atccacgccg gttgagtcgc    2640
gttctgccgc ctcccgcctg tggtgcctcc tgaactgcgt ccgccgtcta ggtaagttta    2700
aagctcaggt cgagaccggg cctttgtccg gcgctccctt ggagcctacc tagactcagc    2760
cggctctcca cgctttgcct gaccctgctt gctcaactct acgtctttgt ttcgttttct    2820
gttctgcgcc gttacagatc aagctgtga ccggcgccta cgctagacgc caccatggag    2880
agcgacgaga gcggcctgcc cgccatggag atcgagtgcc gcatcaccgg caccctgaac    2940
ggcgtggagt tcgagctggt gggcggcgga gagggcaccc ccaagcaggg ccgcatgacc    3000
aacaagatga gagcaccaa aggcgccctg accttcagcc cctacctgct gagccacgtg    3060
atgggctacg gcttctacca cttcggcacc taccccagcg gctacgagaa ccccttcctg    3120
cacgccatca caacggcgg ctacaccaac acccgcatcg agaagtacga ggacggcggc    3180
gtgctgcacg tgagcttcag ctaccgctac gaggccggcc gcgtgatcgg cgacttcaag    3240
gtggtgggca ccggcttccc cgaggacagc gtgatcttca ccgacaagat catccgcagc    3300
aacgccaccg tggagcacct gcaccccatg ggcgataacg tgctggtggg cagcttcgcc    3360
cgcaccttca gcctgcgcga cggcggctac tacagcttcg tggtggacag ccacatgcac    3420
ttcaagagcg ccatccaccc cagcatcctg cagaacgggg cccatgtt cgccttccgc    3480 cgcgtggagg agctgcacag caacaccgag ctgggcatcg tggagtacca gcacgccttc    3540
aagaccccca tcgccttcgc cagatcccgc gctcagtcgt ccaattctgc cgtggacggc    3600
accgccggac ccggctccac cggatctcgc gagggcagag gaagtcttct aacatgcggt    3660
gacgtggagg agaatcccgg ccctatgacc gagtacaagc ccacggtgcg cctcgccacc    3720
cgcgacgacg tccccagggc cgtacgcacc ctcgccgccg cgttcgccga ctaccccgcc    3780
acgcgccaca ccgtcgatcc ggaccgccac atcgagcggg tcaccgagct gcaagaactc    3840
ttcctcacgc gcgtcgggct cgacatcggc aaggtgtggg tcgcggacga cggcgccgcg    3900
gtggcggtct ggaccacgcc ggagagcgtc gaagcggggc cggtgttcgc cgagatcggc    3960
ccgcgcatgg ccgagttgag cggttcccgg ctggccgcgc agcaacagat ggaaggcctc    4020
ctggcgccgc accggcccaa ggagcccgcg tggttcctgg ccaccgtcgg cgtctcgccc    4080
gaccaccagg gcaagggtct gggcagcgcc gtcgtgctcc ccggagtgga ggcggccgag    4140
cgcgccgggg tgcccgcctt cctggagacc tccgcgcccc gcaacctccc cttctacgag    4200
cggctcggct tcaccgtcac cgccgacgtc gaggtgcccg aaggaccgcg cacctggtgc    4260
atgacccgca gcccggtgc ctgaaatcaa cctctggatt acaaaatttg tgaaagattg    4320
actggtattc ttaactatgt tgctcctttt acgctatgtg gatacgctgc tttaatgcct    4380
ttgtatcatg ctattgcttc ccgtatggct ttcatttcct cctccttgta taaatcctgg    4440
ttgctgtctc tttatgagga gttgtggccc gttgtcaggc aacgtggcgt ggtgtgcact    4500
gtgtttgctg acgcaacccc cactggttgg ggcattgcca ccacctgtca gctcctttcc    4560
gggactttcg ctttccccct ccctattgcc acggcggaac tcatcgccgc ctgccttgcc    4620
```

```
cgctgctgga caggggctcg gctgttgggc actgacaatt ccgtggtgtt gtcggggaag    4680
ctgacgtcct ttccatggct gctcgcctgt gttgccacct ggattctgcg cgggacgtcc    4740
ttctgctacg tcccttcggc cctcaatcca gcggaccttc cttcccgcgg cctgctgccg    4800
gctctgcggc ctcttccgcg tctccgcctt cgccctcaga cgagtcggat ctcccttcgg    4860
ccgcctcccc gcctggtacc tttaagacca atgacttaca aggcagctgt agatcttagc    4920 cacttttta aagaaaaggg gggactggaa gggctaattc actcccaacg aaaataagat    4980 ctgcttttg cttgtactgg gtctctctgg ttagaccaga tctgagcctg ggagctctct    5040
ggctaactag ggaacccact gcttaagcct caataaagct tgccttgagt gcttcaagta    5100
gtgtgtgccc gtctgttgtg tgactctggt aactagagat ccctcagacc cttttagtca    5160
gtgtggaaaa tctctagcag tagtagttca tgtcatctta ttattcagta tttataactt    5220
gcaaagaaat gaatatcaga gagtgagagg aacttgttta ttgcagctta taatggttac    5280
aaataaagca atagcatcac aaatttcaca aataaagcat ttttttcact gcattctagt    5340
tgtggtttgt ccaaactcat caatgtatct tatcatgtct ggctctagct atcccgcccc    5400
taactccgcc cagttccgcc cattctccgc cccatggctg actaattttt tttatttatg    5460
cagaggccga ggcgcctcg gcctctgagc tattccagaa gtagtgagga ggcttttttg    5520
gaggcctaga cttttgcaga gacgcccaa attcgtaatc atggtcatag ctgtttcctg    5580
tgtgaaattg ttatccgctc acaattccac acaacatacg agccgaagc ataaagtgta    5640 aagcctgggg tgcctaatga gtgagctaac tcacattaat tgcgttgcgc tcactgcccg    5700
ctttccagtc gggaaacctg tcgtgccagc tgcattaatg aatcggccaa cgcgcgggga    5760
gaggcggttt gcgtattggg cgctcttccg cttcctcgct cactgactcg ctgcgctcgg    5820
tcgttcggct gcggcgagcg gtatcagctc actcaaaggc ggtaatacgg ttatccacag    5880 aatcaggggga taacgcagga aagaacatgt gagcaaaagg ccagcaaaag gccaggaacc    5940
gtaaaaaggc cgcgttgctg gcgttttcc ataggctccg ccccctgac gagcatcaca    6000 aaaatcgacg ctcaagtcag aggtggcgaa acccgacagg actataaaga taccaggcgt    6060
ttccccctgg aagctccctc gtgcgctctc ctgttccgac cctgccgctt accggatacc    6120
tgtccgcctt tctcccttcg ggaagcgtgg cgctttctca tagctcacgc tgtaggtatc    6180
tcagttcggt gtaggtcgtt cgctccaagc tgggctgtgt gcacgaaccc cccgttcagc    6240
ccgaccgctg cgccttatcc ggtaactatc gtcttgagtc aacccggta agacacgact    6300 tatcgccact ggcagcagcc actggtaaca ggattagcag agcgaggtat gtaggcggtg    6360
ctacagagtt cttgaagtgg tggcctaact acggctacac tagaaggaca gtatttggta    6420
tctgcgctct gctgaagcca gttaccttcg gaaaaagagt tggtagctct tgatccggca    6480
aacaaaccac cgctggtagc ggtggttttt tgtttgcaa gcagcagatt acgcgcagaa    6540 aaaaggatc tcaagaagat cctttgatct tttctacggg gtctgacgct cagtggaacg    6600
aaaactcacg ttaagggatt ttggtcatga gattatcaaa aaggatcttc acctagatcc    6660
ttttaaatta aaaatgaagt tttaaatcaa tctaaagtat atatgagtaa acttggtctg    6720
acagttacca atgcttaatc agtgaggcac ctatctcagc gatctgtcta tttcgttcat    6780
ccatagttgc ctgactcccc gtcgtgtaga taactacgat acgggagggc ttaccatctg    6840
gccccagtgc tgcaatgata ccgcgagacc cacgctcacc ggctccagat ttatcagcaa    6900
taaaccagcc agccggaagg gccgagcgca agtggtcc tgcaacttta tccgcctcca    6960
tccagtctat taattgttgc cgggaagcta gagtaagtag ttcgccagtt aatagtttgc    7020
```

```
gcaacgttgt tgccattgct acaggcatcg tggtgtcacg ctcgtcgttt ggtatggctt    7080
cattcagctc cggttcccaa cgatcaaggc gagttacatg atcccccatg ttgtgcaaaa    7140
aagcggttag ctccttcggt cctccgatcg ttgtcagaag taagttggcc gcagtgttat    7200
cactcatggt tatggcagca ctgcataatt ctcttactgt catgccatcc gtaagatgct    7260
tttctgtgac tggtgagtac tcaaccaagt cattctgaga atagtgtatg cggcgaccga    7320
gttgctcttg cccggcgtca atacgggata ataccgcgcc acatagcaga actttaaaag    7380
tgctcatcat tggaaaacgt tcttcggggc gaaaactctc aaggatctta ccgctgttga    7440
gatccagttc gatgtaaccc actcgtgcac ccaactgatc ttcagcatct tttactttca    7500
ccagcgtttc tgggtgagca aaaacaggaa ggcaaaatgc cgcaaaaaag gaataaggg     7560 cgacacggaa atgttgaata ctcatactct tcctttttca atattattga agcatttatc    7620
agggttattg tctcatgagc ggatacatat ttgaatgtat ttagaaaaat aaacaaatag    7680
gggttccgcg cacatttccc cgaaaagtgc cacctgacgt ctaagaaacc attattatca    7740
tgacattaac ctataaaaat aggcgtatca cgaggccctt tcgtctcgcg cgtttcggtg    7800
atgacggtga aaacctctga cacatgcagc tcccggagac ggtcacagct tgtctgtaag    7860
cggatgccgg gagcagacaa gcccgtcagg gcgcgtcagc gggtgttggc gggtgtcggg    7920
gctggcttaa ctatgcggca tcagagcaga ttgtactgag agtgcaccat atgcggtgtg    7980
aaataccgca cagatgcgta aggagaaaat accgcatcag gcgccattcg ccattcaggc    8040
tgcgcaactg ttgggaaggg cgatcggtgc gggcctcttc gctattacgc cagctggcga    8100
aagggggatg tgctgcaagg cgattaagtt gggtaacgcc agggttttcc cagtcacgac    8160
gttgtaaaac gacggccagt gccaagctg                                      8189

<210> SEQ ID NO 6
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 6
ttagcagcgg aacaaggagt                                                  20

<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 7
agccgagaga aaacagtcca                                                  20

<210> SEQ ID NO 8
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(23)
```

<400> SEQUENCE: 8
gcctctccaa gcccaatgga aac                                          23

<210> SEQ ID NO 9
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(23)

<400> SEQUENCE: 9
gcctctccaa gcccaatgga aac                                          23

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 10
ctacggcaga gaacccagag                                              20

<210> SEQ ID NO 11
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 11
ttgatgccag cagaagtcag                                              20

<210> SEQ ID NO 12
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 12
aaggtgaagg tcggagtcaa                                              20

<210> SEQ ID NO 13
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)

<400> SEQUENCE: 13
gatctcgctc ctggaagatg                                              20

<210> SEQ ID NO 14
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(21)

<400> SEQUENCE: 14
aggaggaggg cagaatcatc a                                              21

<210> SEQ ID NO 15
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(21)

<400> SEQUENCE: 15
ctcgattgga tggcagtagc t                                              21

<210> SEQ ID NO 16
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(33)

<400> SEQUENCE: 16
aaagactagt cttgtaaact tgagttggag tac                                 33

<210> SEQ ID NO 17
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(38)

<400> SEQUENCE: 17
aaaagagctc ttttgtattt gagtattgtt ttattaac                            38

<210> SEQ ID NO 18
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(28)

<400> SEQUENCE: 18
gccaactagt accagaaggc caagtccg                                       28

<210> SEQ ID NO 19
<211> LENGTH: 34
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (1)..(34)

<400> SEQUENCE: 19
ggccgagctc tagctgtttt ccaaaatata tttg                                   34
```